United States Patent [19]

Sitzmann et al.

[11] Patent Number: 4,849,540
[45] Date of Patent: Jul. 18, 1989

[54] PENTAFLUOROTHIO POLYNITROALIPHATIC EXPLOSIVES

[75] Inventors: Michael E. Sitzmann, Adelphi; William H. Gilligan, Ft. Washington, both of Md.

[73] Assignee: The United States of America as represented by the Secretary of the Navy, Washington, D.C.

[21] Appl. No.: 213,039

[22] Filed: Jun. 24, 1988

[51] Int. Cl.$^4$ ............................................. C07C 161/00
[52] U.S. Cl. ...................... 560/156; 149/88; 560/159; 562/840
[58] Field of Search ..................... 560/159, 156; 260/543 H, 543 F

[56] References Cited

U.S. PATENT DOCUMENTS 3,102,903 9/1963 Coffman ................ 260/481

OTHER PUBLICATIONS

Tullock, J. Am. Chem. Soc., 86, pp. 357-361, (1964).
Wessel, Chem. Ber., 116, pp. 2399-2407, (1983).

*Primary Examiner*—Michael L. Shippen
*Attorney, Agent, or Firm*—Kenneth E. Walden; Roger D. Johnson

[57] ABSTRACT

Explosive compounds of the formulas

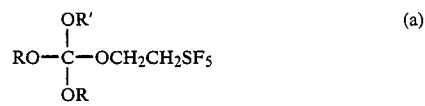 (a)

where R is $-CH_2C(NO_2)_2CH_3$, $-CH_2C(NO_2)_3$, $-CH_2CF(NO_2)_2$, or $-CH_2CF_2(NO_2)$ and R' is $-CH_2CF(NO_2)_2$ or $-CH_2CF_2(NO_2)$;

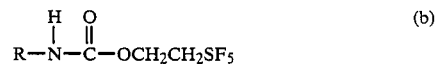

(b)

where R is $-CH_2C(NO_2)_3$ or $-CH_2CF(NO_2)_2$;

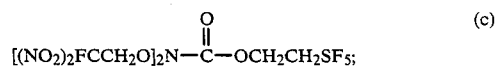

(c)

and

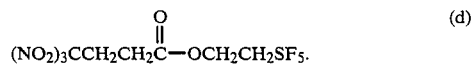 (d)

14 Claims, No Drawings

PENTAFLUOROTHIO POLYNITROALIPHATIC EXPLOSIVES

BACKGROUND OF THE INVENTION

This invention relates to explosives and more particularly to polynitroorganic explosives.

E. F. Witucki and M. B. Frankel, J. Chem. and Eng. Data, 24, 382 (1979), reported the preparation of 2-fluoro-2,2-dinitroethyl pentafluorothioacetate from 2-fluoro-2,2-dinitroethanol and pentafluorothioacetyl chloride. The acetyl chloride was chosen as the $-SF_5$ starting material because of its availability from $SF_5Cl$ and ketene. E. F. Witucki and M. B. Frankel, Rockwell International UCRL report 13809 (1978), describe 2-fluoro-2,2-dinitroethyl pentafluorothioacetate as a dense, thermally stable, insensitive liquid.

We have recently prepared other polynitroaliphatic esters of pentafluorothioacetic acid (using the Witucki et al. method) and have found them to be liquids or very low melting solids. For instance:

| Ester | m.p. (°C.) |
|---|---|
| 2,2-dinitropropyl pentafluorothioacetate | 22 |
| 3-fluoro-3,3-dinitropropyl pentafluorothioacetate | 28 |
| 3,3,3-trinitropropyl pentafluorothioacetate | 32 |

Thus, like the prior art 2-fluoro-2,2-dinitroethyl pentafluorothioacetate, these novel polynitroaliphatic esters of pentafluorothioacetic acid are limited to liquids or very low melting solids. This is a disadvantage because many applications require high melting solid explosives.

Therefore, it would be desirable to have available higher melting pentafluorothio ($SF_5$) explosives in order to provide a greater choice of physical properties for these types of compounds.

SUMMARY OF THE INVENTION

Accordingly, an object of this invention is to provide new energetic explosive compounds.

Another object of this invention is to provide new pentafluorothio polyaliphatic explosives.

A further object of this invention is to provide new high melting pentafluorothio polyaliphatic explosives.

Still another object of this invention is to provide new high energy, high density explosives.

A still further object of this invention is to provide new high energy explosives having good thermal stabilities.

These and other objectives of this invention are achieved by providing:

explosive compounds of the formulas:

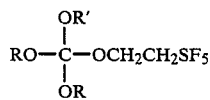  (a)

where R is $-CH_2C(NO_2)_2CH_3$, $-CH_2C(NO_2)_3$, $-CH_2CF(NO_2)_2$, or $-CH_2CF_2(NO_2)$ and R' is $-CH_2CF(NO_2)_2$ or $-CH_2CF_2(NO_2)$;

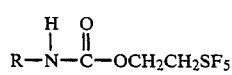  (b)

where R is $-CH_2C(NO_2)_3$ or $-CH_2CF(NO_2)_2$;

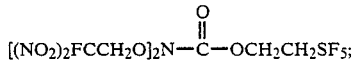  (c)

and

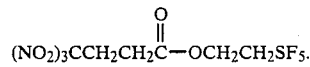  (d)

DETAILED DESCRIPTION OF THE PREFERRED EMBODIMENT

This invention provides new high energy, high density, high melting explosives which contain both pentafluorothioethyl, $-CH_2CH_2SF_5$, groups and polynitroaliphatic groups. These compounds are prepared by the reaction of pentafluorothioethanol, $F_5SCH_2CH_2OH$, with selected polynitroaliphatic reactants. The pentafluorothioethanol can be prepared by the reduction of pentafluorothioacetyl chloride with lithium aluminum hydride

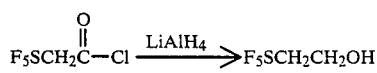

as illustrated by example 1 using a method disclosed by J. Wessel, G. Kleemann and K. Seppelt, Chem. Ber., 116(7), 2399 (1983). The pentafluorothioacetyl chloride can be prepared from $SF_5Cl$ and ketene using the method disclosed in Example II, column 5, of U.S. Pat. No. 3,102 903 entitled "Carbonylic Compounds Containing the $SF_5$ Function," which issued to Donald D. Coffman and Charles W. Tullock on Sept. 3, 1963, herein incorporated by reference.

The pentafluorothioethanol is reacted with chloroorthoformates of the formula

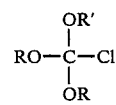

to produce orthocarbonates of the formula

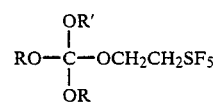

where R is $-CH_2C(NO_2)_2CH_3$, $-CH_2C(NO_2)_3$, $-CH_2CF(NO_2)_2$, or $-CH_2CF_2(NO_2)$ and R' is $-CH_2CF(NO_2)_2$ or $-CH_2CF_2(NO_2)$. Specifically, (1) tris(2-fluoro-2,2-dinitroethyl)(2-pentafluorothioethyl) orthocarbonate, $[CF(NO_2)_2CH_2O]_3-C-OCH_2CH_2SF_5$;

(2) tris(2,2-difluoro-2-nitroethyl)(2-pentafluorothioethyl) orthocarbonate, $[CF_2(NO_2)CH_2O]_3-C-OCH_2CH_2SF_5$;

(3) bis(2,2-dinitropropyl)(2-fluoro-2,2-dinitroethyl)(2-pentafluorothioethyl) orthocarbonate,

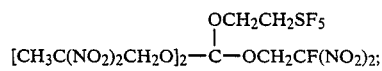

(4) bis(2,2-dinitropropyl)(2,2-difluoro-2-nitroethyl) (2-pentafluorothioethyl) orthocarbonate,

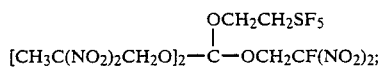

5) bis(2,2,2-trinitroethyl) (2-fluoro-2,2-dinitroethyl) (2-pentafluorothioethyl)orthocarbonate,

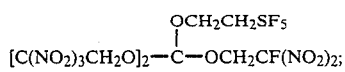

(6) bis(2,2,2-trinitroethyl)(2,2-difluoro-2-nitroethyl) (2-pentafluorothioethyl)orthocarbonate,

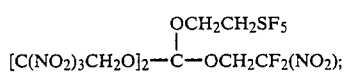

(7) bis(2,2-difluoro-2-nitroethyl)(2-fluoro-2,2-dinitroethyl) (2-pentafluorothioethyl)orthocarbonate,

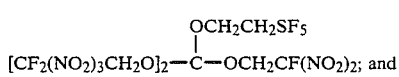

(8) bis(2-fluoro-2,2-dinitroethyl)(2,2-difluoro-2nitroethyl) (2-pentafluorothioethyl) orthocarbonate,

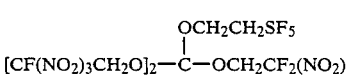

are prepared from the corresponding chlorothoformates
(1) $[CF(NO_2)_2CH_2O]_3CCl$,
(2) $[CF_2(NO_2)CH_2O]_3CCl$,
(3) $[CH_3C(NO_2)_2CH_2O]_2CCl-OCH_2CF(NO_2)_2$,
(4) $[CH_3C(NO_2)_2CH_2O]_2CCl-OCH_2CF_2(NO_2)$,
(5) $[C(NO_2)_3CH_2O]_2CCl-OCH_2CF(NO_2)_2$,
(6) $[C(NO_2)_3CH_2O]_2CCl-OCH_2CF_2(NO_2)$,
(7) $[CF_2(NO_2)CH_2O]_2CCl-OCH_2CF(NO_2)_2$, and
(8) $[CF(NO_2)_2CH_2O]_2CCl-OCH_2CF_2(NO_2)$,
respectively. The reaction is carried out according to the method illustrated in example 3.

The chloroorthoformates are prepared by reacting the corresponding trichloromethyl disulfide compounds with chlorine gas

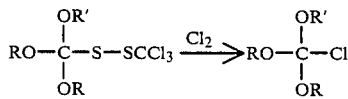

as illustrated by example 2 and as also disclosed in U.S. Pat. No. 4,449,000 entitled, "1:1:2 And 1:3 Mixed Polynitroethyl Orthocarbonates Via Mixed Trialkoxymethyl Trichloromethyl Disulfides," which issued to Michael E. Sitzmann and William H. Gilligan on May 15, 1984, herein incorporated by reference. The required disulfide compounds, $[CF(NO_2)_2CH_2O]_3CSSCCl_3$, (1)
$[CF_2(NO_2)CH_2O]_3CSSCCl_3$, (2)

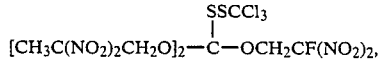 (3)

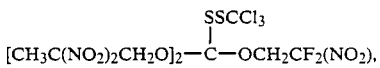 (4)

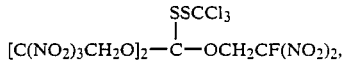 (5)

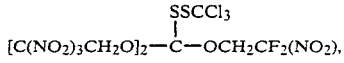 (6)

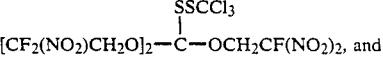 (7)

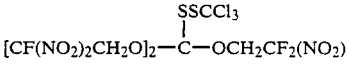 (8)

are prepared by reacting the appropriate thiocarbonate selected from
(a) $[CH_3C(NO_2)_2CH_2O]_2-C=S$,
(b) $[C(NO_2)_3CH_2O]_2-C=S$,
(c) $[CF(NO_2)_2CH_2O]_2-C=S$, and
(d) $[CF_2(NO_2)CH_2O]_2-C=S$
with the appropriate alcohol selected from
(e) $CF(NO_2)_2CH_2OH$ and
(f) $CF_2(NO_2)CH_2OH$
and with $ClSCCl_3$ according to the general reaction $(RO)_2-C=S + R'OH + ClSCCl_3 \xrightarrow{NaOH}$ $(RO)_2(RO')CSSCCl_3$.

The reaction conditions are taught by the Sitzmann et al. (U.S. Pat. No. 4,449,000), herein incorporated by reference. Bis(2-fluoro-2,2-dinitroethyl)thiocarbonate, $[CF(NO_2)_2CH_2O]_2-C=S$, can be prepared from 2-fluoro-2,2-dinitroethanol and thiophosgene using the method disclosed in U.S. Pat. No. 4,172,088 entitled "Bis(2-fluoro-2,2-dinitroethyl)thionocarbonate and a Method of Preparation," which issued to Isaac A. Angres et al. on Oct. 23, 1979, herein incorporated by reference. The remaining thionocarbonates can be synthesized from thiophosgene and the appropriate alcohol using the method disclosed in U.S. Pat. No. 4,323,518 entitled "Polynitroethylthionocarbonates and Method of Preparation," which issued to William H. Gilligan on Apr. 6, 1982, herein incorporated by reference. Carbamates of the formula

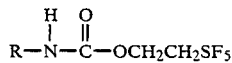

are prepared by reacting one mole of an isocyanate $R-N=C=O$ with one mole of 2-pentafluorothioethanol, where R is $-CH_2C(NO_2)_3$ or $-CH_2CF(NO_2)_2$, according to the reaction conditions disclosed in Example 4. In Example 4 one mole of 2,2,2-trinitroethyl isocyanate is reacted with one mole of 2-pentafluorothioethanol to produce N-(2,2,2-trinitroethyl)(2-pentafluorothioethyl) carbamate. The 2,2,2-trinitroethyl isocyanate starting material is produced according to the reaction sequence given in examples 7, 8, 9, and 10. By reacting one mole of 2-fluoro-2,2-dinitroethyl isocyanate with one mole of 2-pentafluorothioethanol, N-(2-fluoro-2,2-dinitroethyl) (2-pentafluorothioethyl) carbamate will be produced. The 2-fluoro-2,2-dinitroethyl isocyanate starting material can be produced according to a method disclosed in example 12.

N,N-Bis(2-fluoro-2,2-dinitroethyl)(2-pentafluorothioethyl) carbamate can be prepared by reacting one mole of N,N-bis(2-fluoro-2,2-dinitroethyl)carbamyl chloride with one mole of 2-pentafluorothioethanol by the method illustrated in example 5. The N,N-bis(2-fluoro-2,2-dinitroethyl)carbamyl chloride starting material can be prepared according to the method disclosed in examples 1 and 2 of U.S. Pat. No. 4,311,649 entitled, "N,N-bis(2-fluoro-2,2-dinitroethyl) Carbamate Esters," which issued on Jan. 19, 1982 to William H. Gilligan and Michael E. Sitzmann, herein incorporated by reference.

Finally, Example 6 illustrates the preparation of 2-pentafluorothioethyl 4,4,4-trinitrobutyrate by reacting one mole of 4,4,4-trinitrobutyric acid with one mole of 2-pentafluorothioethanol with concentrated sulfuric acid at reflux.

The general nature of the invention having been set forth the following examples are presented as specific illustrations thereof. It will be understood that the invention is not limited to these specific examples, but is susceptible to various modifications that will be recognized by one of ordinary skill in the art Example 1 was run according to a method disclosed by J. Wessel, G. Kleemann, and K. Seppelt, Chem. Ber., 116(7), 2399 (1983).

EXAMPLE 1

Pentafluorothioethanol (prior art)

Pentafluorothioacetyl chloride 24 ml, 41.4 g) in 120 ml of dry ether (distilled from lithium aluminum hydride) was added dropwise to a mixture of 9.2 g of lithium aluminum hydride and 200 ml of dry ether stirred in a water bath at 15°–25° C. The mixture was stirred at reflux temperature for 1 hr before it was cooled in an ice bath and water (12 ml) was slowly added dropwise (the mixture became very thick). After the mixture was stirred at room temperature for 15 min., it was again cooled in ice and a cold solution of 18 ml of concentrated sulfuric acid in 120 ml of water was added. After standing overnight, essentially all solid material had dissolved. The ether layer was separated and the aqueous phase was extracted with 3 ×60 ml of ether. The ether extracts were combined, dried over magnesium sulfate and most of the ether was removed by distillation through a vigreaux column (water bath temperature reached 70° C. before distillation was stopped). Methylene chloride (100 ml) was added and then removed through a vigreaux column. This was repeated with 100 ml of methylene chloride and then the liquid residue was pulled under vacuum (water aspirator) for a short time to give 32.1 g (92%) of 2-pentafluorothioethanol. The product was combined with 100 ml of dry 1,2-dichloroethane and the solution was dried over 50 g of 3 Å molecular sieves for 3 days before the sieves were removed by filtration and washed with 3×50 ml of dry dichlorethane. The filtrate (280 ml) was then stored over 10 g of 3 Å molecular sieves for at least one day before use.

Example 2 was run according to a method disclosed in our U.S. Pat. No. 4,449,000.

EXAMPLE 2 tris(2-fluoro-2,2-dinitroethyl)chloroorthoformate (prior art method)

Dry chlorine gas was passed for 2 hrs into a solution of 81.0 g (0.124 mole) of tris(2-fluoro-2,2-dinitroethoxy)methyl trichloromethyl disulfide in 300 ml of dry 1,2-dichloroethane at 60°–65° C. The solution was allowed to stand at ambient temperature overnight before the volatiles were removed with a stream of nitrogen and heating at 60°–65° C. The cooled residue was stirred with 300 ml of dry hexanes to give tris(2-fluoro-2,2-dinitroethyl)chloroorthoformate as an insoluble white solid. The hexanes solution was decanted from the solid which was washed with hexanes.

EXAMPLE 3

Tris(2-fluoro-2,2-dinitroethyl) (2-pentafluorothioethyl) orthocarbonate

The tris(2-fluoro-2,2-dinitroethyl)chloroorthoformate product from example 2 was dissolved in 150 ml of dry 1,2-dichloroethane. A solution (195 ml) of 22.3 g (0.129 mole) of 2-pentafluorothioethanol in 1,2-dichloroethane was added and the reaction solution was heated for 8 hr at reflux temperature. The volatiles were removed to give 74.2 g of residue which was dissolved in 150 ml of warm chloroform. The hot solution was treated with charcoal, filtered and the filter pad was washed with 3×30 ml of hot chloroform. Hexanes (100 ml) was slowly added followed by cooling to −20° C. to give 58.8.g (74%) of crystals, mp 95°–97° C. Recrystallization from chloroform-hexanes raised the melting point to 96°–97° C.;

$^1$H NMR (CDCl$_3$): 3.7 to 4.2 (broad m, 4H), 4.76 (d, 6H);

IR (KBR): 1615 (NO$_2$), 880–800 (SF$_5$) cm$^{-1}$.

Anal. Calcd for C$_9$H$_{10}$F$_8$N$_6$O$_{16}$S: C, 16.83; H, 1.57; F, 23.66; N, 13.08; S, 4.99. Found: C, 16.89; H, 1.60; F, 23.11; N, 12.11; S, 5.14.

EXAMPLE 4

N-(2,2,2-Trinitroethyl)(2-pentafluorothioethyl) carbamate

A solution of 1.2 g (0.0058 mole) of 2,2,2-trinitroethyl isocyanate, 1.0 g (0.0058 mole) of 2-pentafluorothioethanol and 10 mg of iron (III) 2,4-pentanedionate in 8 ml of 1,2-dichloroethane was heated at 80° C. for 1 hr. The cooled solution was decanted from a small amount of dark insoluble material before the volatiles were removed to give an oil which was chromatographed on silica gel 40 (methylene chloride as eluent) to give 1.93 g (88%) of product, mp 76°–79° C. Crystallization from methylene chloride-hexanes gave 1.60 g (73%), mp 81°–82° C.;

$^1$H NMR (CDCl$_3$): 3.95 (m, 2H), 4.63 (t, 2H), 4.93 (d, 2H), 5.6 (broad, 1H).

IR (KBr): 3460, 3320 (NH), 1725 (C=O), 1610 (NO$_2$), 900–800 (SF$_5$) cm$^{-1}$.

Anal. Calcd for C$_5$H$_7$F$_5$N$_4$O$_8$S: C, 15.88; H, 1.86; F, 25.12; N, 14.81; S, 8.48. Found: C, 15.92; H, 1.86; F, 25.06; N, 14.58; S, 8.80.

EXAMPLE 5

N,N-Bis(2-fluoro-2,2-dinitroethyl)(2-pentafluorothioethyl) carbamate

To a solution of 0.70 g (0.002 mole) of N,N-bis(2-fluoro-2,2dinitroethyl) carbamyl chloride and 0.45 g (0.0026 mole) of 2-pentafluorothioethanol in 3 ml of dry methylene chloride stirred in an ice bath was added 0.2 ml of pyridine. After 3 hr at room temperature 4 ml of 10% hydrochloric acid was added and the methylene chloride layer was separated and dried over sodium sulfate. Removal of the volatiles gave an oil which was chromatographed on silica gel 60 (methylene chloride as eluent) to give 0.45 g (46%) of essentially pure product. Crystallization from chloroform-hexanes gave crystals, mp 61°–62° C.;

$^1$H NMR (CDCl$_3$): 3.90 (m, 2H), 4.60 (t, 2H), 4.82 (d, 4H);

IR (KBr):1745 (C=O), 1620 (NO$_2$), 900–800 (SF$_5$).

Anal Calcd for C$_7$H$_8$F$_7$N$_5$O$_{10}$S: C, 17.26; H, 1.66; F, 27.30; N, 14.37; S, 6.58. Found: C, 17.30; H, 1.63; F, 27.82; N, 14.25; S, 6.57.

EXAMPLE 6

2-Pentafluorothioethyl 4,4,4-Trinitrobutyrate

A mixture of 0.55 g (0.0025 mole) of 4,4,4-trinitrobutyric acid, 0.47 g (0.0027 mole) of 2-pentafluorothioethanol and 0.3 ml of conc. sulfuric acid in 9 ml of 1,2-dichloroethane was stirred at reflux temperature for 2 hr in a flask with a reverse Dean Stark trap attached. The cooled reaction mixture was decanted from the insoluble sulfuric acid before the volatiles were removed to give a dark oil which was chromatographed on silica gel 40 using methylene chloride as eluent. The product was 0.81 g (86%) of solid, mp 44°–46° C. Crystallization from chloroform-hexanes raised the melting point to 45°–46° C.;

$^1$H NMR (CDCl$_3$): 2.83 (t, 2H), 3.47 (t, 2H), 3.97 (m, 2H), 4.64 (t, 2H).

Anal. Calcd for C$_6$H$_8$F$_5$N$_3$SO$_8$: C, 19.10; H, 2.14; F, 25.18; N, 11.14; S, 8.50. Found: C, 19.19; H, 2.10; F, 24.82; N, 11.05; S, 8.48.

Examples 7, 8, 9, and 10 provide a sequence for synthesizing 2,2,2-trinitroethyl isocyanate which was used as a starting material in example 4. The procedure used in example 7 is essentially that reported by: Salmon, *J. Prakt Chem.*, 1873, 7, 256 (Berlstein, III, 138). Examples 8, 9, and 10 are taken from our (Michael E. Sitzmann and William H. Gilligan) article, "Novel Route from Thiocarbamate to Isocyanate: 2,2,2-Trinitroethyl Isocyanate," *J. Org. Chem.*, (1985), 50, 5879–5881 at 5880.

EXAMPLE 7

S-Ethyl Thiocarbamate (prior art)

Gaseous ammonia was slowly passed into a solution of 30 ml (36 g, 0.29 mole) of ethyl chlorothiolformate (tech. grade 95%) in 180 ml of methylene chloride until the mixture contained excess ammonia (wet litmus paper) The temperature was kept below 10° C. during the addition of ammonia by cooling in an ice bath. The large amount of white precipitate formed was removed by filtration and the solvent was removed from the filtrate to give additional product. The combined product was washed with 50 ml of water to remove ammonium chloride and then was dissolved in water at 60° C. Cooling to 5° C. gave 21.8 g (72%) of white crystals, m.p. 107–108. Lit. m.p. 107–108 (Beilstein 3, 138).

EXAMPLE 8

S-Ethyl N-(2,2,2-Trinitroethyl)Thiocarbamate (prior art)

"To 21 g (0.116 mol) of 2,2,2-trinitroethanol in 110 mL of water was added 10 g of potassium acetate, 15 mL of acetic acid, 9 mL of 36% aqueous formaldehyde, and 12.2 g (0.116 mol) of S-ethyl thiocarbamate. The mixture was heated in an oil bath at 70°–75° C. for five h before it was cooled in an ice bath and the insoluble oil (18 g) was extracted into methylene chloride. The oil was chromatographed on silica gel 40 (115 g) using methylene chloride as eluent to give 8.6 g (28%) of crystals, mp 61°–63° C.:

$^l$H-NMR (CDCl$_3$): 1.29 (t, 3 H), 2.98 (q, 2 H), 4.98 (d, 2 H), 6.00 (br, 1 H); IR (KBr): 3280 (NH), 1665 (C=O), 1595 (NO$_2$) cm$^{-1}$.

Anal. Calcd for C$_5$H$_8$N$_4$O$_7$S: C, 22.39; H, 3.01; N, 20.89; S, 11.95. Found: C, 22.50; H, 2.99; N, 20.79; S, 12.07."

EXAMPLE 9

N-(2,2,2-Trinitroethyl)carbamyl Chloride (prior art)

"To a stirred solution of 1.01 g (6.9 mmol) of benzenesulfenyl chloride in 2 mL of dry 1,2-dichloroethane was added 1.80 g (6.9 mmol) of 4 [S-ethyl N-(2,2,2trinitroethyl)thiocarbamate]. After 30 min the volatiles were removed at 25° C. with a stream of nitrogen, 5 mL of hexane was added (oil separated), and the mixture was cooled to $-10°$ C. to yield a solid. The solution was decanted from the solid, which was then washed with hexane and quickly dried in a vacuum desiccator over drierite to give 1.36 g (84%), m.p. 56°–58° C.:

$^l$H-NMR (CDCl$_3$) 4.90 (d, 2 H), 6.43 (br, 1 H); IR (film) 3420, 3320 (NH), 1765 (C=O), 1600 (NO$_2$) cm$^{-1}$."

Upon standing overnight in the vacuum desiccator, an appreciable amount of the solid had turned to an oil. The IR spectrum then showed a large isocyanate absorption at 2275 cm$^{-1}$."

EXAMPLE 10

2,2,2-Trinitroethyl Isocyanate (prior art)

"A solution of 5 [N-(2,2,2-trinitroethyl)carbamyl chloride](1.36 g, 5.6 mmol), in 15 mL of dry carbon tetrachloride was heated in an oil bath at 75° for three h. During the heating period a slow stream of nitrogen was swept over the solution and out the condenser (protected by a drierite drying tube) to remove evolved hydrogen chloride and force the reaction to completion. After the 3 h heating period, the volatiles were removed with a rapid stream of nitrogen to give 1.0 g(87%) of 1 -[2,2,2-trinitroethyl isocyanate]as an oil:

$^1$H-NMR (C$_6$D$_6$): 5.40 (s);

IR (film): 2380, 2275 (N=C=O), 1600 (NO$_2$) cm$^{-1}$."

The following example for the preparation of 2-fluoro-2,2dinitroethyl isocyanate is quoted from Horst G. Adolph, "Fluoronitroaliphatics. VI. Preparation of N-(2,2,2-Fluorodinitroethyl)amides," J. Org. Chem 37, 747 at 750 (1972).

EXAMPLE 11

2-fluoro-2,2-dinitroethyl isocyanate

"To a solution of 6 g of phosgene in 50 ml of methylene chloride was added dropwise at 0°–5° and with stirring a solution of 9.2 g of 1 [2-fluoro-2,2-dinitroethylamine]and 6.2 g of triethylamine in 25 ml of methylene chloride. After the exothermic reaction had subsided, another 6.2 g of triethylamine was added dropwise and the mixture was stirred at room temperature for 1 hr, filtered rapidly, and freed from solvent in vacuo. The liquid portion of the remaining semisolid material was dissolved in methylene chloride - hexane (1:1), and the solution was filtered and concentrated. Vacuum distillation of the remaining oil gave 2 g of 6 [2-fluoro-2,2-dinitroethyl isocyanate]as a pale yellow liquid, bp ca. 45° (0.1 mm), exhibiting a single peak in the glpc chromatogram and a strong band in the ir at 2250 cm$^{-1}$..."

Examples 12, 13 and 14 present three novel polynitroaliphatic esters of pentafluorothioacetic acid which were prepared according to a method disclosed by E. F. Witucki and M. B. Frankel in Rockwell International UCRL report 13809. The pentafluorothioacetic acid starting material can be prepared according to a method disclosed by D. D. Coffman and C. W. Tullock in U.S. Pat. No. 3,102,903, herein incorporated by reference.

EXAMPLE 12

3,3,3-Trinitropropyl Pentafluorothioacetate

A mixture of 0.57 g (0.003 mole) of pentafluorothioacetic acid, 1.2 g (0.006 mole) of 3,3,3-trinitropropanol and 0.3 ml of concentrated sulfuric acid in 10 ml of 1,2-dichloroethane was stirred at reflux temperature for 24 hr in a flask with a reverse Dean Stark trap attached. The reaction mixture was cooled and the organic layer was decanted from the insoluble sulfuric acid. After the removal of volatiles from the organic layer, the residue (oil) was chromatographed on silica gel 40 using methylene chloride as eluent to give 0.99 g (89%) of product, mp 32° C.;

$^1$H NMR (CDCl$_3$): 3.52 (broad t, 2H), 4.35 (quintet, 2H), 4.70 (t, 2H);

IR (film): 1870 (C=O), 1605 (NO$_2$), 920–800 (SF$_5$).

Anal. Calcd for C$_5$H$_6$F$_5$N$_3$O$_8$S: C, 16.54; H, 1.66; F, 26.16; N, 11.56; S, 8.83. Found: C, 16.44; H, 1.67; F, 26.01; N, 11.19; S, 8.84.

EXAMPLE 13

2,2-dinitropropyl pentafluorothioacetate

Using a method similar to example 12, 2,2-dinitropropanol and pentafluorothioacetic acid were reacted to form 2,2-dinitropropyl pentafluorothioacetate (95% yield) mp 22° C.;

$^1$H NMR (CDCl$_3$): 2.27 (s, 3H), 4.40 (quintet, 2H), 5.10 (s, 2H);

IR (film): 1775 (C=O), 1580 (NO$_2$), 920–800 (SF$_5$).

Anal. Calcd for C$_5$H$_7$F$_5$N$_2$O$_6$S: C, 18.87; H, 2.22; F, 29.86; N, 8.80; S, 10.08. Found: C, 18.90; H, 2.28; F, 29.74; N, 8.75; S, 10.03.

EXAMPLE 14

3-fluoro-3,3-dinitropropyl pentafluorothioacetate

Using a method similar to example 12, 3-fluoro-3,3-dinitropropanol and pentafluorothioacetic acid were reacted to form 3-fluoro-3,3-dinitropropyl pentafluorothioacetate (83% yield) mp 28° C.;

$^1$H NMR (CDCl$_3$): 3.17, 3.37 (d of t, 2H), 4.30 (quintet, 2H), 4.55 (t, 2H);

IR (film): 1770 (C=O), 1605 (NO$_2$), 920–800 (SF$_5$).

Anal. Calcd for C$_5$H$_6$F$_6$N$_2$O$_6$S: C, 17.86; H, 1.80; F, 33.91; N, 8.33; S, 9.53; Found: C, 17.85; H, 1.92; F, 34.12; N, 8.32; S, 9.45.

As demonstrated by examples 12 through 14, polynitroaliphatic esters of pentafluorothioacetic acid have low melting points which make them unsuitable for most applications.

Obviously, numerous modifications and variations of the present invention are possible in light of the above teachings. It is therefore to be understood that within the scope of the appended claims the invention may be practiced otherwise than as specifically described herein.

What is claimed and desired to be secured by Letters Patent of the United States is:

1. An orthocarbonate of the formula

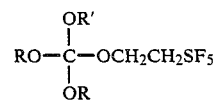

wherein R is selected from the group consisting of —CH$_2$C(NO$_2$)$_2$CH$_3$, —CH$_2$C(NO$_2$)$_3$, —CH$_2$CF(NO$_2$)$_2$, and —CH$_2$CF$_2$(NO$_2$), and wherein R' is selected from the group consisting of —CH$_2$CF(NO$_2$)$_2$ and —CH$_2$CF$_2$(NO$_2$).

2. The orthocarbonate of claim 1 which is tris(2-fluoro-2,2-dinitroethyl)(2-pentafluorothioethyl) orthocarbonate, [CF(NO$_2$)$_2$CH$_2$O]$_3$—C—OCH$_2$CH$_2$SF$_5$.

3. The orthocarbonate of claim 1 which is tris(2,2-difluoro-2-nitroethyl)(2-pentafluorothioethyl) orthocarbonate, [CF$_2$(NO$_2$)CH$_2$O]$_3$—C—OCH$_2$CH$_2$SF$_5$.

4. The orthocarbonate of claim 1 which is bis(2,2dinitropropyl)(2-fluoro-2,2-fluoro-2,2-dinitroethyl)(2-pentafluorothioethyl) orthocarbonate,

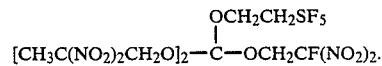

5. The orthocarbonate of claim 1 which is bis(2,2-dinitropropyl)(2,2-difluoro-2-nitroethyl) (2-pentafluorothioethyl) orthocarbonate,

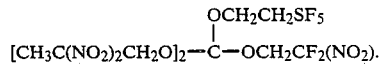

6. The orthocarbonate of claim 1 which is bis(2,2,2-trinitroethyl)(2-fluoro-2,2-dinitroethyl)(2-pentafluorothioethyl) orthocarbonate,

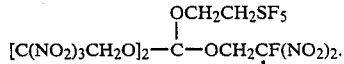

7. The orthocarbonate of claim 1 which is bis(2,2,2-trinitroethyl) (2,2-difluoro-2-nitroethyl)(2-pentafluorothioethyl) orthocarbonate,

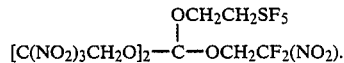

8. The orthocarbonate of claim 1 which is bis(2, 2-difluoro-2-nitroethyl) (2-fluoro-2,2-dinitroethyl) (2-pentafluorothioethyl) orthocarbonate,

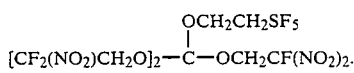

9. The orthocarbonate of claim 1 which is bis(2-fluoro-2, 2-dinitroethyl) (2,2-difluoro-2-nitroethyl)(2-pentafluorothioethyl) orthocarbonate,

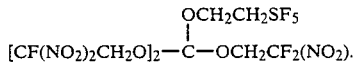

10. A carbamate of the formula

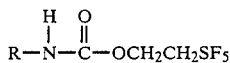

wherein R is selected from the group consisting of —CH$_2$C(NO$_2$)$_3$ and —CH$_2$CF(NO$_2$)$_2$.

11. The carbamate of claim 10 which is N-(2,2,2-trinitroethyl) (2-pentafluorothioethyl)carbamate,

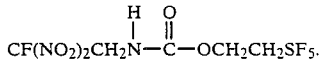

12. The carbamate of claim 10 which is N-(2-fluoro-2,2-dinitroethyl) (2-pentafluorothioethyl)carbamate,

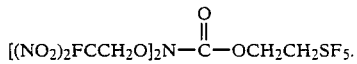

13. N,N-bis(2-fluoro-2,2-dinitroethyl)(2-pentafluorothioethyl) carbamate,

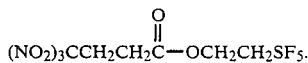

14. 2-pentafluorothioethyl 4,4,4-trinitrobutyrate, $$\underset{\|}{\overset{O}{(NO_2)_3CCH_2CH_2C}}-OCH_2CH_2SF_5.$$

* * * * *